United States Patent [19]

Atanassova et al.

[11] Patent Number: 4,933,454
[45] Date of Patent: Jun. 12, 1990

[54] ACYLUREIDOAMINOTHIAZOLYL DERIVATIVES AND A METHOD FOR THEIR PREPARATION

[75] Inventors: Tashka K. Atanassova; Anton I. Nakov; Lyudmila V. Petkova; Zoya T. Ivanova; Donka M. Mondeshka, all of Sofia, Bulgaria

[73] Assignee: Technologitchen Kombinat za Promishlena Mikrobologia, Razgrad, Bulgaria

[21] Appl. No.: 341,092

[22] Filed: Apr. 20, 1989

[51] Int. Cl.$^5$ ............................................ C07D 417/12
[52] U.S. Cl. .................................... 544/369; 548/195; 548/196
[58] Field of Search ................. 548/195, 196; 544/369

[56] References Cited
U.S. PATENT DOCUMENTS 4,473,577 9/1984 Sakano et al. ...................... 514/371
4,490,393 12/1984 Sakano et al. ...................... 514/371

OTHER PUBLICATIONS

Yamanouchi Pharm. Co. Ltd., Chem. Abst. 103-104958e (1985).

Primary Examiner—Cecilia Shen
Attorney, Agent, or Firm—Klein & Vibber

[57] ABSTRACT

The invention concernes acylureidoaminothiazolyl derivatives possessing pharmacological activity and a method for preparing them.

2-aminothiazolyl derivatives having an allyl radical with 1-4 carbon atoms are known in the pharmaceutical practice as immunomodulators, active against immune failure diseases.

The aim of the invention is to synthesize new 2-aminothiazolyl derivatives possessing pharmacological activity and describe a new method for their preparation.

11 Claims, No Drawings

ACYLUREIDOAMINOTHIAZOLYL DERIVATIVES AND A METHOD FOR THEIR PREPARATION

FIELD OF THE INVENTION

According to the invention new acylureidoaminothiazolyl derivatives of the general formula I are prepared:

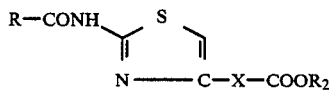

where R means a group of the formula:

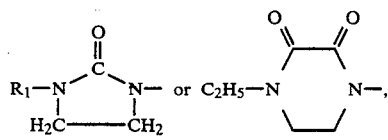

$R_1$—H or $CH_3SO_2$-group
$R_2$—H or lower alkyl group

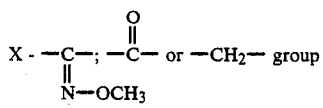

The new acylureidoaminothiazolyl derivatives are prepared by acylating compounds of general formula:

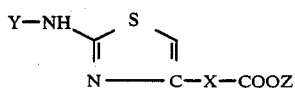

where
X has the above meanings;
Z is H, lower alkyl or —Si(CH$_3$)$_3$
Y is H or —Si(CH$_3$)$_3$
with compounds of formula:

R—COCl    III where R has the above meaning in an anhydrous medium in the presence of a hydrogen chloride acceptor at a temperature of the reaction medium from 0° C. to the temperature of boiling of the solvent in which the acylation takes place.

As organic solvents in which the process of acylation can be carried out in halogenated hydrocarbons such as methylene chloride, chloroform, carbon tetrachloride; esters of lower fatty acids such as ethyl acetate, butyl acetate; lower dialkyl ketones—acetone, methylethyl ketone; cyclic esters—tetrahydrofurane; benzene, toluene, etc. can be used.

When compounds of formula II in which Y=Z have the meaning of —Si(CH$_3$)$_3$ or N is H and Z is —Si(CH$_3$)$_3$ are used, these compounds are obtained by the known methods of silylation with the usual silylating agents well known in the field.

As hydrogen chloride acceptors triethylamine, dimethylaniline, pyridine, etc.; or a mixture of N-silyl- derivatives of the corresponding amides or ureas and triethylammonium chloride can be used.

The components of the reaction can take part in the process or acrylation in equimolar quantities or, in order to increase the yield of the final product and for more economical consumption of the compounds of formula II, the carbamoylchlorides can be dosed in an excess of 0.1 to 0.3 moles according to the organic solvent and the conditions in which the the reaction takes place. The unreacted carbamoylchlorides in the process of isolation of the corresponding acylureidoaminothiazolyl derivatives are transformed into neutral products easily soluble in water, which simplifies the isolation and the purification of the final product.

The acylation of the compounds of general formula II can be carried out in a wide temperature interval—from 0° C. to the boiling point of the corresponding solvent for a time of 2 to 28 hours. The low temperatures decrease the yield of the reaction.

The conditions, under which the process of acylation is carried out, as well as the isolation of the prepared aminothiazolyl compounds, according to the invention, ensure the retaining of the "syn" configuration of the initial product of formula II, where X is

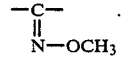

The new acylureidoaminothiazolyl derivatives possess antiinflammatory properties.

The following examples further illustrate the invention.

EXAMPLE 1

Methyl ester of the 2-[2-(2-oxo-imidazolidine-1-carboxamido)-thiazol-4-yl]-2-syn-methoxyimino acetic acid.

4.3 g (20 mmols) of the methyl ester of 2-(2-aminothiazol-4-yl)-2-methoxyimino acetic acid are added to 60 ml of methylenechloride. The mixture is cooled to a temperature of 0°-5° C. and 3.3 ml of triethylamine and 3.5 g (24 mmols) of 1-chlorcarbonylimidazolydon-2 are added. It is heated to reflux for 4 hours, then cooled to ambient temperature and filtered. The filtrate is washed first with dilute hydrochloric acid, then with aqueous sodium bicarbonate and then water. It is dried over anhydrous sodium sulphate and concentrated under reduced pressure. The product is precipitated by the addition of di-isopropyl ether, 5.7 g are obtained.

$C_{11}N_{12}N_5O_5$ (327.31); calc.,% C 40.36, H 4.00, N 21.40, found,% C 40.38, H 4.11, N 21.44.

$^1$H—NMR data (CDCl$_3$): δ(ppm): 3.18, 3.60 (4H, m), —4CH$_2$ and —5CH$_2$; 3.65(3H, s) and 3.85 (3H, s), —COOCH$_3$ and —NOCH$_3$; 7.04 (1H, s), —H$_5$; 7.70 (1H, s, wide), —2CONH; 11.10 (1H, s), wide, —2-CONH IR data (KBr): 3300, 3180, 1720, 1690, 1525, 1260, 1020 cm$^{-1}$

EXAMPLE 2

Methyl ester of 2-[2-(4-ethyl-2,3-dioxo-1-piperazine carboxamido)-thiazol-4-yl]-2-syn-methoxyimino acetic acid.

This compound is prepared, according to the method, described in example 1 by the reaction of 4.3 g (20 mmols) methyl ester of 2-(2-aminothiazol-4-yl)-2-methoxyiminoacetic acid, 3.6 ml (26 mmols) of triethylamine and 5.3 g (26 mmols) 4-ethyl-2,3-dioxopiperazinylcarbonyl chloride. The reaction mixture, after concentrating under reduced pressure is passed through a silica gel chromatographic column. The product is eluated with ethyl acetate-tetrahydrofurane. The eluate is concentrated under reduced pressure. 5.8 g of the product are isolated.

$C_{14}H_{17}N_5O_6S$ (383.38) calc.% C 43.86, H 4.47, N 18.27, found,% C 43.77, H 4.39, N 18.31.

$^1$H—NMR data (CDCl$_3$): δ(ppm): 1.14 (3H, t) and 3.36 (2H, q), —N—C$_2$H$_5$; 3.45 (2H, m) and 4.00 (2H, m), —5CH$_2$ and —6CH$_2$; 3.73 (3H, s), and 3.85(3H, s), —N—OCH$_3$ and —COOCH$_3$; 6.94 (1H, s), 11.82 (1H, wide, exchanges with D$_2$O), —2—CONH;

IR data (KBr): 3400, 3180, 1730, 1690, 1438, 1525, 1720, 1280, 1038 cm$^{-1}$

EXAMPLE 3

2-[2-(2-oxo-imidazolidine-1-carboxamido)-thiazol-4-yl]-2-syn-methoxyimino acetic acid.

To a suspension of 4.0 g (20 mmols) 2-(2-aminothiazol-4-yl)-2-methoxyimino acetic acid in 30 ml of chloroform are added 67 ml (44 mmols) of triethylamine and 5.6 ml (44 mmols) of trimethylchlorsilane. The reaction mixture is refluxed with stirring for three hours and then filtered. After cooling to −5° C. to the filtrate are added 2.9 ml (21 mmols) triethylamine and 3.19 (21 mmols) 1-chlor-carbonylimidazolidone-2. The reaction mixture is stirred 8 hours at ambient temperature and filtered. 30 ml of water are added to the filtrate and the stirring is continued for another 20 minutes. The pH of the mixture is corrected to 1.5 and the layers are separated. The chloroform layer is washed first with dilute hydrochloric acid and then with water, dried over anhydrous magnesium sulphate and concentrated under reduced pressure.

5 g of the above named product are obtained.

$C_{10}H_{11}N_5O_5$ (313.29) calc.,% C 38.34, H 3.54, N 22.38, found,% C 38.39, H 3.61, N 22.41.

$^1$H—NMR data (DMSO-d$_6$): δ(ppm): 3.26 and 3.72 (4H, m), —4′-CH$_2$ and 5′-CH$_2$; 3.72 (3H, s), —N—OCH$_3$; 7.16 (1H, s), —N—5; 7.82 (1H, s, exchanges with D$_2$O) —2′-CONH; 11.24 (1H, s-wide, exchanges with D$_2$O)—2-CONH.

EXAMPLE 4

2-[2-(4-ethyl-2,3-dioxo-1-piperazinecarboxamido)-thiazol-4-yl]-2-syn-methoxyimino acetic acid.

4.6 ml (22 mmols) of hexamethyldisilazane is added to a suspension of 4.0 g (20 mmols) of 2-(2-aminothiazol-4-yl)-2-methoxyimino acetic acid in 15 ml of methylenechloride. The mixture is refluxed with stirring for 4 hours, after which it is cooled to a temperature of −5° C. 3.0 ml (22 mols) triethylamine and 4.5 g (22 mmols) 4-ethyl-2,3-dioxopiperazine carbonylchloride are added to the cooled reaction mixture. The stirring is continued for six hours at ambient temperature and then filtered. 30 ml of water are added and the mixture is hydrolysed for 20 minutes, after which the pH is corrected to 1.5 and the layers are separated. The organic layer is concentrated under reduced pressure and the crude product is chromatographed on a silica gel column. It is eluated with chloroform-tetrahydrofurane (18:2) and on concentrating of the eluate 5.6 g. of the product are obtained.

$C_{13}H_{15}N_5O_6S$ (369.38) calc.,% C 42.28, H 4.09, N 18.96, found, % C 42,25, H 4.12, N 18.77.

$^1$H—NMR data (DMSO-d$_6$): δ(ppm): 1.17 (3H, t) and 3.40 (2H, q), —N—C$_2$H$_5$; 3.50 (2H, m) and 4.08 (2H, m), —5′-CH$_2$′ and 6′-CH$_2$; 3.72 (3H, s), 7.02 (1H, s), 11.6 (1H, s-wide, exchanges with D$_2$O), —2-CONH.

EXAMPLE 5

Ethyl ester of 2-[2-(2-oxo-imidazolidine-1-carboxamido)-thiazol-4-yl]-acetic acid This compound is prepared according to the method, described in ex. 1 by the reaction of 1.9 g (10 mmols) of ethyl-2-(2-aminothiazol-4-yl)acetate with 1.6 g (11 mmols) 1-chlorcarbonylimidazolidone-2 in the presence of 1.5 ml (11 mmols) triethylamine as a hydrogen chloride acceptor. 2.2 g of the product are obtained.

$C_{11}H_{14}N_4O_4$ (298.31) calc.% C 44.29, H 4.73, N 18.78, found,% C 44.32, 4.80, N 18.82.

$^1$H—NMR data (DMSO-d$_6$): δ(ppm): 1.10 (3H, t) and 3.9 (2H, q), —OC$_2$H$_5$; 3.47 (2H, s), —4CH$_2$; 3.24 and 3.69 (4H, m), —4′-CH$_2$ and 5′-CH$_2$; 6.67 (1H, s), H-5 7.75 (1H, s, wide), —2′-CONH; 11.13(1H, s-wide, exchanges with D$_2$O), —2-CONH.

IR data (KBr): 3295, 3175, 1735, 1720, 1680, 1410, 1425, 1435, 1350, 1250, 1020 cm$^{-1}$

EXAMPLE 6

Ethyl ester of 2-[2-(4-ethyl-2,3-dioxo-1-piperazinecarboxamido)-thiazol-4-yl]-acetic acid The compound is prepared according to the method, described in ex. 2 by the reaction of 1.9 g (10 mmols) of ethyl 2-(2-aminothiazol-4-yl) acetate with 2.7 g (13 mmols) of 4-ethyl-2,3-dioxo-1-piperazinecarbonylchloride in the presence of 1.8 ml (13 mmols) triethylamine as an acceptor of hydrogen chloride.

2.9 g of the product are produced.

$C_{14}H_{18}N_4O_5S$ (354.34) calc.,% C 47.45, H 5.12, N 15.81, found,% C 47.48, H 5.11, N 15.79.

$^1$H—NMR data (DMSO-d$_6$): δ(ppm): 1.03 (3H, t) and 3.27 (2H, q), —N—C$_2$H$_5$; 1.12 (3H, t) and 3.92 (2H, q), —COOC$_2$H$_5$; 3.50 and 3.88 (4H, m), —5′-CH$_2$ and —6′-CH$_2$; 3.54 (2H, s), —4-CH$_2$; 6.81 (1H, s), H-5 11.28 (1H, s-wide, exchanges with D$_2$O), —CONH.

IR data (KBr): 3390, 1710, 1680, 1520, 1410, 1425, 1435, 1350, 1285, 1138 cm$^{-1}$

EXAMPLE 7

2-[2-(2-oxo-imidozolidine-1-carboxamido)-thiazol-4-yl]-acetic acid

The compound is prepared according to the method, described in ex. 3, by sililating 3.2 g (20 mmols) of 2-(2-aminothiazol-4-yl)-acetic acid with 5.6 ml (44 mmols) trimethylchlorsilane in the presence of 6.1 ml (44 mmols) triethylamine as hydrogen, chloride acceptor and next acylating the obtained silyl ester with 3.1 g (21 mmols) 1-chlorcarbonylimidazolidone-2. Yield 3.9 g.

$C_9H_{10}N_4O_4S$ (270.26) calc.,% C 39.99, H 3.73, N 20.73, found,% C 40.01, H 3.78, N 20.76.

$^1$H—NMR data (DMSO-d$_6$): δ(ppm): 3.53 (3H, s), 3.28 (2H, q) and 3.72 (4H, m), —4′-CH$_2$ and 5′-CH$_2$; 6.67 (1H, s), —H-5; 7.78 (1H, s), wide and 11.13 (1H, s-wide, exchanges with D$_2$O), —2′-CONH and —2-CONH.

EXAMPLE 8

2-[2-(4-ethyl-2,3-dioxo-1-piperazinecarboxamido-(thiazol-4-yl)[-acetic acid

This compound is prepared according to the method, described in ex. 4, by sililating 3.2 g (20 mmols) of 2-(2-aminothiazol-4-yl)-acetic acid with 4.6 ml (22 mmols) hexamethyldisilazane and next acylating the obtained silyl ester with 4.5 g (22 mmols) of 4-ethyl-2,3-dioxo-1-piperazinecarbonylchloride in the presence of a hydrogen chloride acceptor.

Yield 4.8 g.

$C_{12}H_{14}N_4O_5S$ (326.32) calc.,% C 44.17, H 4.32, N 17.17, found,% C 44.21, H 4.35, N 17.27.

$^1$H—NMR data (DMSO-$d_6$): δ(ppm): 1.07 (3H, t), 3.25 (2H, q), —N—$C_2H_5$; 3.35 and 3.78 (4H, m), —5-$CH_2$ and 6'-$CH_2$; 3.54 (2H, s), —4-$CH_2$; 6.81 (2H, s), —H-5; 11.27 (1H, s-wide, exchanges with $D_2O$), —CONH.

EXAMPLE 9

Ethyl ester of the 2-[2-(2-oxo-imidazolidine-1-carboxamido)-thiazol-4-yl]-glyoxalic acid 4.0 g (20 mmols) ethyl ester of the 2-(2-aminothiazol-4-yl)-glyoxalic acid are added to 50 ml of tetrahydrofurane. After cooling to 0°–5° C., 3.2 ml triethylamine and 3.3 g (23 mmols) 1-chlorcarbonylimidazolidone-2 are added and the reaction mixture is refluxed for 5–6 hours. It is then cooled to room temperature, filtered and the tetrahydrofurane is distilled of under reduced pressure. The residue is dissolved in 50 ml chloroform. The chloroform solution, is washed first with dilute hydrochloric acid, then with aqueous sodium bicarbonate and last with water and dried over anhydrous sodium sulphate. After concentrating under reduced pressure the product is precipitated with diisopropyl ether.

Yield 4.6 g.

$C_{11}H_{12}N_4O_5S$ (312.30) calc.,% C 42.30, H 3.87, N 17.94, found,% C 42.43, H 3.92, N 18.03.

$^1$H—NMR data (DMSO-$d_6$): δ(ppm): 1.22 (3H, t) and 4.19 (2H, q), —O$C_2H_5$; 3.24 and 3.27 (4H, m), —4'-$CH_2$ and 5'-$CH_2$; 8.15 (1H, s), —H-5; 7.90 (1H, s-wide), and 11.58 (1H,-wide, exchanges with $D_2O$) —2'-CONH and 2-CONH,

EXAMPLE 10

Ethyl ester of 2-[2-(4-ethyl-2,3-dioxo-1-piperazinecarboxamido)-thiazol-4-yl]-glyoxalic acid The compound is prepared, according to the method, described in ex. 9, by the reaction of 4.0 g (20 mmols) ethyl ester of 2-(2-aminothiazol-4-yl)-glyoxalic acid, 3.3 ml (24 mmols) triethylamine and 4.9 g (24 mmols) of 4-ethyl-2,3-dioxo-1-piperazinecarbonylchloride. The chloform solution after concentration under reduced pressure is passed through a chromatographic column, filled with silicagel. The eluate is evaporated under vacuum.

Yield 6.1 g.

$C_{14}H_{16}N_4O_6S$ (368.36) calc.,% C 45.65, H 4.38, N 15.21, found,% C 45.74, H 4.41, N 15.17.

$^1$H—NMR data-(DMSO-$d_6$): δ(ppm): 1.05 (3H, t) and 3.30 (2H, q), —N—$C_2H_5$; 1.25 (3H, t) and 4.18 (2H, q), —COO$C_2H_5$; 3.50 (2H, m) and 3.89 (2H, m), —5'$CH_2$ and 6'-$CH_2$ 3.18 (1H, s), —H-5; 11.68 (1H, s-wide, exchanges with $D_2O$), —CONH.

EXAMPLE 11

The results of the antiinflammatory action (Carrageenine edema) of the new acylureidoaminothiazolyl derivates by the method of Winter et al are shown in tables 1, 2, 3, 4, 5, 6.

TABLE 1

Methyl ester of 2-[2-(2-oxo-imidazolydine-1-carboxamido)-thiazol-4-yl]-2-syn-methoxyimino acetic acid (example 1)

| Dose | Start. value | 1 h | 2 h | 3 h | 4 h | 5 h | 24 h |
|---|---|---|---|---|---|---|---|
| 1 mg | 1 | 1.29 | 1.52 | 1.58 | 1.67 | 1.59 | 1.41 |
|  |  | 129% | 152% | 158% | 167% | 159% | 141% |
| 3 mg | 0.96 | 1.40 | 1.37 | 1.57 | 1.66 | 1.57 | 1.38 |
|  |  | 146% | 143% | 164% | 173% | 164% | 144% |
| 5 mg | 1.06 | 1.31 | 1.46 | 1.64 | 1.72 | 1.73 | 1.23 |
|  |  | 123% | 138% | 154% | 166% | 165% | 115% |
| 10 mg | 1.04 | 1.21 | 1.27 | 1.47 | 1.61 | 1.58 | 1.17 |
|  |  | 116% | 122% | 141% | 155% | 152% | 113% |
| blank | 0.91 | 1.28 | 1.58 | 1.72 | 1.77 | 1.80 | 1.38 |
|  |  | 141% | 174% | 189% | 195% | 198% | 152% |

TABLE 2

Methyl ester of the 2-[2-(4-ethyl-2,3-dioxo-1-piperazinocarboxamido)-thiazol-4-yl]-2-syn-methoxyimino acetic acid (example 2)

| Dose | Start. value | 1 h | 2 h | 3 h | 4 h | 5 h | 24 h |
|---|---|---|---|---|---|---|---|
| 1 mg | 0.96 | 1.27 | 1.55 | 1.60 | 1.66 | 1.63 | 1.45 |
|  |  | 132% | 161% | 166% | 172% | 169% | 151% |
| 3 mg | 1.0 | 1.39 | 1.40 | 1.57 | 1.67 | 1.62 | 1.35 |
|  |  | 139% | 140% | 157% | 167% | 162% | 135% |
| 5 mg | 1.04 | 1.29 | 1.46 | 1.62 | 1.72 | 1.74 | 1.25 |
|  |  | 124% | 140% | 155% | 165% | 167% | 120% |
| 10 mg | 1.06 | 1.22 | 1.25 | 1.46 | 1.63 | 1.60 | 1.15 |
|  |  | 115% | 117% | 137% | 154% | 151% | 108% |
| blank | 0.92 | 1.29 | 1.61 | 1.71 | 1.77 | 1.83 | 1.43 |
|  |  | 140% | 175% | 185% | 192% | 199% | 155% |

TABLE 3

Ethyl ester of the 2-[2-(2-oxo-imidazolidinecarboxamido)-thiazol-4-yl]-acetic acid (example 5)

| Dose | Start. value | 1 h | 2 h | 3 h | 4 h | 5 h | 24 h |
|---|---|---|---|---|---|---|---|
| 1 mg | 0.87 | 1.23 | 1.36 | 1.39 | 1.53 | 1.47 | 1.16 |
|  |  | 141% | 156% | 160% | 175% | 169% | 133% |
| 3 mg | 0.91 | 1.29 | 1.18 | 1.25 | 1.45 | 1.30 | 1.18 |
|  |  | 142% | 130% | 137% | 159% | 143% | 130% |
| 5 mg | 0.94 | 1.08 | 1.20 | 1.31 | 1.43 | 1.49 | 1.14 |
|  |  | 115% | 128% | 139% | 152% | 159% | 121% |
| 10 mg | 0.95 | 1.06 | 1.20 | 1.33 | 1.46 | 1.54 | 1.07 |
|  |  | 113% | 126% | 140% | 154% | 162% | 113% |
| blank | 0.91 | 1.28 | 1.58 | 1.72 | 1.77 | 1.80 | 1.38 |
|  |  | 141% | 174% | 189% | 195% | 198% | 152% |

TABLE 4

Ethyl ester of the 2-[2-(4-ethyl-2,3-dioxo-1-piperazin-carboxamido)-thazol-4-yl] acetic acid (example 6)

| Dose | Start. value | 1 h | 2 h | 3 h | 4 h | 5 h | 24 h |
|---|---|---|---|---|---|---|---|
| 1 mg | 0.90 | 1.25 | 1.34 | 1.40 | 1.52 | 1.50 | 1.12 |
|  |  | 139% | 149% | 156% | 168% | 166% | 124% |
| 3 mg | 0.92 | 1.30 | 1.30 | 1.32 | 1.47 | 1.38 | 1.12 |
|  |  | 141% | 141% | 142% | 158% | 148% | 120% |
| 5 mg | 0.94 | 1.10 | 1.23 | 1.34 | 1.43 | 1.50 | 1.10 |
|  |  | 117% | 129% | 142% | 152% | 160% | 117% |
| 10 mg | 0.95 | 1.08 | 1.20 | 1.36 | 1.42 | 1.52 | 1.10 |
|  |  | 113% | 126% | 143% | 149% | 160% | 115% |
| blank | 0.93 | 1.31 | 1.69 | 1.75 | 1.80 | 1.85 | 1.35 |
|  |  | 140% | 174% | 188% | 193% | 199% | 146% |

TABLE 5

Ethyl ester of the 2-[2-(2-oxo-imidazoline-1-carboxamido)-thiazol-4-yl]-glyoxalic acid (example 9)

| Dose | Start. value | 1 h | 2 h | 3 h | 4 h | 5 h | 24 h |
|---|---|---|---|---|---|---|---|
| 1 mg | 0.96 | 1.32 | 1.54 | 1.72 | 1.62 | 1.56 | 1.31 |
|  |  | 135% | 160% | 179% | 169% | 163% | 1475 |
| 3 mg | 0.97 | 1.32 | 1.57 | 1.67 | 1.57 | 1.67 | 1.27 |
|  |  | 136% | 162% | 165% | 162% | 172% | 131% |
| 5 mg | 1.11 | 1.38 | 1.63 | 1.73 | 1.75 | 1.69 | 1.34 |
|  |  | 124% | 147% | 158% | 158% | 152% | 121% |
| 10 mg | 1.05 | 1.36 | 1.68 | 1.85 | 1.68 | 1.73 | 1.25 |
|  |  | 130% | 160% | 176% | 1605 | 164% | 119% |
| blank | 1.01 | 1.28 | 1.42 | 1.72 | 1.72 | 1.69 | 1.35 |
|  |  | 127% | 141% | 171% | 171% | 168% | 134% |

TABLE 6

Ethyl ester of teh 2-[2-(4-ethyl-2,3-dioxo-1-piperazin-carboxamido)-thiazol-4-yl]-glyoxalic acid (example 10)

| Dose | Start. value | 1 h | 2 h | 3 h | 4 h | 5 h | 24 h |
|---|---|---|---|---|---|---|---|
| 1 mg | 0.90 | 1.30 | 1.54 | 1.61 | 1.67 | 1.57 | 1.27 |
|  |  | 144% | 171% | 179% | 186% | 174% | 141% |
| 3 mg | 0.95 | 1.15 | 1.26 | 1.55 | 1.59 | 1.64 | 1.21 |
|  |  | 121% | 133% | 163% | 167% | 173% | 127% |
| 5 mg | 0.96 | 1.21 | 1.30 | 1.55 | 1.52 | 1.61 | 1.15 |
|  |  | 126% | 135% | 161% | 158% | 168% | 120% |
| 10 mg | 0.95 | 1.07 | 1.34 | 1.33 | 1.44 | 1.54 | 1.12 |
|  |  | 112% | 141% | 140% | 152% | 162% | 118% |
| blank | 1.01 | 1.28 | 1.42 | 1.72 | 1.72 | 1.69 | 1.35 |
|  |  | 127% | 141% | 171% | 171% | 168% | 134% |

What is claimed is:

1. Acylureidoaminothiazolyl formula I

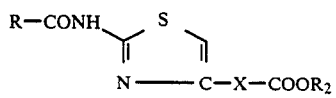

where R denotes a group of formula 1

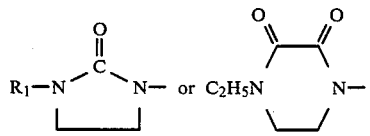

where
R₁ is H or CH₃SO₂-group;
R₂ is H or lower alkyl;
and

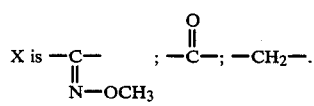

2. The compound of claim 1, being methyl ester of the 2-[2-(2-oxo-imidazoline-1-carboxamido)-thiazol-4-yl]-syn-methoxyimino acetic acid.

3. The compound of claim 1, being the methyl ester of 2-[2-(4-ethyl-2,3-dioxo-1-piperazine carboxamido)-thiazol-4-yl]-2-syn-methoxyimino acetic acid.

4. The compound of claim 1, being 2-[2-(2-oxo-imidazolidine-1-carboxamido)-thiazol-4-yl]-2-syn-methoxyimino acetic acid.

5. The compound of claim 1, being 2-[2-(4-ethyl-2,3-dioxo-1-piperazinecarboxamido)-thiazol-4-yl]-2-syn-methoxyimino acxetic acid.

6. The compound of claim 1, being the ethyl ester of 2-[2-(2-oxo-imidazolidine-1-carboxamido)-thiazol-4-yl]-acetic acid.

7. The compound of claim 1, being the ethyl ester of 2-[2-(4-ethyl-2,3-dioxo-1-piperazinecarboxamido-(thiazol-4-yl)-acetic acid.

8. The compound of claim 1, being 2-[2-(2-oxo-imidazolidine-1-carboxamido)-thiazol-4-yl]-acetic acid.

9. The compound of claim 1, being 2-[2-(4-ethyl-2,3-dioxo-1-piperazine-carboxamido)-thiazol-4-yl)-acetic acid.

10. The compound of claim 1, being the ethyl ester of 2-[2-(imidazolidine-1-carboxamido)-thiazol-4-yl]-glyoxalic acid.

11. The compound of claim 1, being the ethyl ester of [2-(4-ethyl-2,3-dioxo-1-piperazine-carboxamido)-thiazol-4-yl)-glyoxalic acid.

* * * * *

UNITED STATES PATENT AND TRADEMARK OFFICE
CERTIFICATE OF CORRECTION

PATENT NO. : 4,933,454

DATED : June 12, 1990

INVENTOR(S) : Tashka K. ATANASSOVA, Anton L. NAKOV, Lyudmila V. PETKOVA, Zoya T. IVANOVA and Donka M. MONDESHKA It is certified that error appears in the above-identified patent and that said Letters Patent are hereby corrected as shown below:

Cover page, item [73], line 2, delete "Mikrobologia" and substitute therefor —Mikrobiologia—.

Signed and Sealed this

Third Day of September, 1991

*Attest:*

HARRY F. MANBECK, JR.

*Attesting Officer*       *Commissioner of Patents and Trademarks*